US008877984B2

(12) United States Patent
Barton et al.

(10) Patent No.: US 8,877,984 B2
(45) Date of Patent: Nov. 4, 2014

(54) PROCESS FOR THE PREPARATION OF 1,3-CYCLOHEXANEDIMETHANOL FROM ISOPHTHALIC ACID

(75) Inventors: Benjamin Fredrick Barton, Kingsport, TN (US); Steven Leroy Cook, Kingsport, TN (US); Jeff Scott Howell, Jonesborough, TN (US); Noah Glenn McMillan, Kingsport, TN (US); Damon Bryan Shackelford, Kingsport, TN (US); Brent Alan Tennant, Church Hill, TN (US); Phillip Wayne Turner, Blountville, TN (US)

(73) Assignee: Eastman Chemical Company, Kingsport, TN (US)

(*) Notice: Subject to any disclaimer, the term of this patent is extended or adjusted under 35 U.S.C. 154(b) by 239 days.

(21) Appl. No.: 13/476,219

(22) Filed: May 21, 2012

(65) Prior Publication Data
US 2013/0030222 A1    Jan. 31, 2013

Related U.S. Application Data

(60) Provisional application No. 61/513,087, filed on Jul. 29, 2011.

(51) Int. Cl.
| C07C 31/133 | (2006.01) |
| C07C 67/08 | (2006.01) |
| C07C 29/149 | (2006.01) |
| C07C 67/303 | (2006.01) |
| C07C 29/80 | (2006.01) |

(52) U.S. Cl.
CPC ............ *C07C 67/08* (2013.01); *C07C 29/149* (2013.01); *C07C 67/303* (2013.01); *C07C 29/80* (2013.01); *C07C 2101/14* (2013.01)
USPC ........................ 568/831; 568/861; 568/864

(58) Field of Classification Search
USPC .................... 568/831, 861, 864, 858
See application file for complete search history.

(56) References Cited

U.S. PATENT DOCUMENTS

| 1,628,190 | A | 5/1927 | Raney |
| 3,334,149 | A | 8/1967 | Akin et al. |
| 5,185,476 | A | 2/1993 | Gustafson |
| 5,387,752 | A | 2/1995 | Scarlett et al. |
| 5,395,987 | A | 3/1995 | Rathmell et al. |
| 5,399,742 | A | 3/1995 | Tennant et al. |
| 6,187,968 | B1 * | 2/2001 | Itoh et al. ............... 568/831 |
| 6,284,703 | B1 | 9/2001 | Ostgard et al. |
| 6,919,489 | B1 * | 7/2005 | McCusker-Orth ............ 568/864 |
| 7,632,962 | B2 * | 12/2009 | Liu ............... 560/127 |
| 8,410,317 | B2 | 4/2013 | Turner et al. |
| 8,410,318 | B2 | 4/2013 | Barton et al. |

FOREIGN PATENT DOCUMENTS

| GB | 988316 A | 4/1965 |
| JP | 2000 001447 A | 1/2000 |

OTHER PUBLICATIONS

Co-pending U.S. Appl. No. 13/194,024, filed Jul. 29, 2011, Phillip Wayne Turner, et al.
Co-pending U.S. Appl. No. 13/194,040, filed Jul. 29, 2011, Brent Alan Tennant, et al.
Co-pending U.S. Appl. No. 13/194,051, filed Jul. 29, 2011, Benjamin Fredrick Barton, et al.
USPTO Office Action dated Jun. 28, 2012 for co-pending U.S. Appl. No. 13/194,051.
USPTO Office Action dated Jun. 29, 2012 for co-pending U.S. Appl. No. 13/194,024.
Notification of Transmittal of The International Search Report and The Written Opinion of The International Searching Authority, or the Declaration with a mailing date of Sep. 11, 2012, International Application No. PCT/US2012/047796.
Notification of Transmittal of the International Search Report and the Written Opinion of the International Searching Authority with a mailing date of Sep. 6, 2012, International Application No. PCT/US2012/047792.
Notification of Transmittal of the International Search Report and the Written Opinion of the International Searching Authority with a mailing date of Sep. 6, 2012, International Application No. PCT/US2012/047793.
Notification of Transmittal of the International Search Report and the Written Opinion of the International Searching Authority with a mailing date of Sep. 11, 2012, International Application No. OCT/US2012/047795.
USPTO Office Action dated Jun. 14, 2013 for co-pending U.S. Appl. No. 13/194,040.
USPTO Notice of Allowance received in U.S. Appl. No. 13/194,040 dated Feb. 25, 2014.

* cited by examiner

*Primary Examiner* — Sudhakar Katakam
*Assistant Examiner* — Pancham Bakshi
(74) *Attorney, Agent, or Firm* — Eric D. Middlemas; Louis N. Moreno

(57) ABSTRACT

Disclosed is a process for the preparation of 1,3-cyclohexanedimethanol from isophthalic acid. Isophthalic acid is esterified with (3-methylcyclohexyl)methanol and the isophthalate ester hydrogenated to 1,3-cyclohexanedimethanol in a 2-stage process. The (3-methylcyclohexyl)methanol that is formed during the hydrogenation step is recycled to the esterification reaction. Also disclosed is a method for purifying and recovering the 1,3-cyclohexanedimethanol product.

26 Claims, No Drawings

PROCESS FOR THE PREPARATION OF 1,3-CYCLOHEXANEDIMETHANOL FROM ISOPHTHALIC ACID

CROSS REFERENCES TO RELATED APPLICATIONS

This application claims the benefit of U.S. Provisional Application Ser. No. 61/513,087 filed Jul. 29, 2011.

FIELD OF THE INVENTION

This invention pertains to a process for the preparation of 1,3-cyclohexanedimethanol by esterification of isophthalic acid and the subsequent catalytic hydrogenation of the isophthalate diester. More particularly, this invention pertains to a process for the preparation of 1,3-cyclohexanedimethanol in which the by-products of the hydrogenation process are recycled as raw materials for the preparation of the isophthalate diester feedstock and in which the purification of the 1,3-cyclohexanedimethanol product is simplified.

BACKGROUND OF THE INVENTION

Cyclohexanedimethanols are important intermediates for producing a variety of polyesters for coatings, fibers, molding plastics, packaging materials, and the like. Cyclohexanedimethanols are typically manufactured by the hydrogenation of the corresponding cyclohexanedicarboxylate esters. For example, one of the more commercially important cyclohexanedimethanols, 1,4-cyclohexanedimethanol (abbreviated herein as "CHDM"), typically is prepared by a two-step hydrogenation process involving hydrogenation of dimethyl isophthalate (abbreviated herein as "DMT"), to give dimethyl 1,4-cyclohexanedicarboxylate (abbreviated herein as "DMCD"), followed by hydrogenation of the ester groups. The various steps of this process have been described, for example, in U.S. Pat. Nos. 3,334,149, 6,919,489; 5,399,742; 5,387,752; 5,395,987; 5,185,476; and 7,632,962; and United Kingdom Patent Application No. 988,316. The preparation of 1,3-cyclohexanedimethanol (abbreviated herein as "1,3-CHDM") can be carried out in an analogous manner by hydrogenation of dimethylisophthalate (abbreviated herein as "DMI") to dimethyl cyclohexane-1,3-dicarboxylate that can be further hydrogenated to 1,3-CHDM.

The use of DMI as starting material for the preparation of 1,3-CHDM presents several challenges. DMT is typically prepared by the esterification of isophthalic acid with methanol under high pressures and temperatures. DMI must also be distilled prior to its introduction into the hydrogenation step of the 1,3-CHDM process in order to remove partial esterification products and any esterification catalysts that can poison and/or reduce the activity of the downstream hydrogenation catalysts. Finally, the hydrogenation of DMI releases methanol that requires additional purification and processing steps in order to recover and recycle the methanol from the 1,3-CHDM hydrogenation product mixtures. The use of alternative 1,3-CHDM feedstocks that avoid these difficulties, therefore, could greatly improve the efficiency and reduce the equipment and processing costs of the 1,3-CHDM process.

SUMMARY OF THE INVENTION

It has been discovered that 1,3-cyclohexanedimethanol may be efficiently prepared in a simplified process that comprises the preparation of the bis(3-methycyclohexyl)methanol diester of isophthalic acid and by hydrogenation of this ester to produce the 1,3-CHDM. One embodiment of our invention, therefore, is a process for the preparation of 1,3-cyclohexanedimethanol from isophthalic acid comprising:

(i). contacting isophthalic acid and (3-methylcyclohexyl) methanol in a mole ratio of alcohol to acid of at least 2:1, in a reaction zone at a temperature of about 150° C. to about 280° C., while removing water from the reaction zone, to form an esterification product mixture comprising bis(3-methylcyclohexyl)methyl)isophthalate and unreacted (3-methylcyclohexyl)methanol;

(ii). contacting the esterification product mixture with hydrogen in a first hydrogenation zone in the presence of a catalyst effective for hydrogenation of an aromatic ring to produce a liquid effluent comprising bis(3-methylcyclohexyl)methyl)cyclohexane-1,3-dicarboxylate;

(iii). contacting the effluent from the first hydrogenation zone with hydrogen in the presence of an ester hydrogenation catalyst in a second hydrogenation zone to produce a hydrogenation product comprising 1,3-cyclohexanedimethanol, 3,3'-oxybis(methylene)bis(methylcyclohexane), and (3-methylcyclohexyl)methanol, and;

(iv). recycling at least a portion of the (3-methylcyclohexyl) methanol from step (iii) to step (i).

In the process of the invention, isophthalic acid is esterified with (3-methylcyclohexyl)methanol (abbreviated herein as "3-MCHM"), which is a by-product of the 1,3-CHDM hydrogenation process, to produce bis(3-methylcyclohexyl)methyl)isophthalate that is then hydrogenated to 1,3-CHDM. The 3-MCHM released during the ester hydrogenation step, therefore, does not introduce any new impurities into the hydrogenation process and can be recycled to the esterification step of the process.

Our inventive process also provides a simplified method of purification of the 1,3-CHDM hydrogenation product mixture. Thus, another embodiment of the invention is a process for the preparation of 1,3-cyclohexanedimethanol, comprising:

(i). contacting bis(3-methylcyclohexyl)methyl)isophthalate with hydrogen in a first hydrogenation zone in the presence of a catalyst effective for hydrogenation of an aromatic ring to produce a liquid effluent comprising bis(3-methylcyclohexyl)methyl)cyclohexane-1,3-dicarboxylate;

(ii). contacting the effluent from the first hydrogenation zone with hydrogen in the presence of an ester hydrogenation catalyst in a second hydrogenation zone to produce a hydrogenation product comprising 1,3-cyclohexanedimethanol, 3,3'-oxybis(methylene)bis(methylcyclohexane), and (3-methylcyclohexyl)methanol;

(iii). distilling the hydrogenation product from step (ii) to recover a distillate comprising a majority of the (3-methylcyclohexyl)methanol in the hydrogenation product and a distillation bottoms comprising a majority of the 1,3-cyclohexanedimethanol and 3,3'-oxybis(methylene)bis(methylcyclohexane) in the hydrogenation product;

(iv). allowing the distillation bottoms to form a lower layer comprising a majority of the 1,3-cyclohexanedimethanol in the distillation bottoms and a upper layer comprising a majority of the 3,3'-oxybis(methylene)bis(methylcyclohexane) in the distillation bottoms; and (v). separating the upper and lower layers of step (iv) and recovering the 1,3-cyclohexanedimethanol from the lower layer by distillation.

After removal of at least a portion of the 3-MCHM present in the crude 1,3-CHDM hydrogenation mixture, the distillation bottoms separates into an upper layer containing the diether of 3-MCHM and many of the impurities present in the hydrogenation product and a lower layer comprising most of the 1,3-CHDM product. Most of the by-products produced during the hydrogenation step, therefore, can be removed by a simple separation of the upper and lower layers.

The esterification and purification steps of our process can be combined to provide an integrated process for 1,3-CHDM in which the 3-MCHM by-product from the hydrogenation step is recycled to the IPA esterification step as the alcohol feedstock. Yet another aspect of the invention, therefore, is a process for the preparation of a 1,3-cyclohexanedimethanol from isophthalic acid, comprising:

(i). contacting isophthalic acid and (3-methylcyclohexyl)methanol in a mole ratio of alcohol to acid of at least 2:1, in a reaction zone at a temperature of about 170° C. to about 280° C. while removing water from the reaction zone, to form an esterification product mixture comprising bis(3-methylcyclohexyl)methyl)isophthalate and unreacted (3-methylcyclohexyl)methanol;

(ii). contacting the esterification product mixture with hydrogen in a first hydrogenation zone in the presence of a catalyst effective for hydrogenation of an aromatic ring to produce a liquid effluent comprising bis(3-methylcyclohexyl)methyl)cyclohexane-1,3-dicarboxylate;

(iii). contacting the effluent from the first hydrogenation zone with hydrogen in the presence of an ester hydrogenation catalyst in a second hydrogenation zone to produce a hydrogenation product comprising 1,3-cyclohexanedimethanol, 3,3'-oxybis(methylene)bis(methylcyclohexane), and (3-methylcyclohexyl)methanol;

(iv). distilling the hydrogenation product from step (iii) to recover a distillate comprising a majority of the (3-methylcyclohexyl)methanol in the hydrogenation product and a distillation bottoms comprising a majority of the 1,3-cyclohexanedimethanol and 3,3'-oxybis(methylene)bis(methylcyclohexane) in the hydrogenation product;

(v). allowing the distillation bottoms to form an lower layer comprising a majority of the 1,3-cyclohexanedimethanol in the distillation bottoms and a upper layer comprising a majority of the 3,3'-oxybis(methylene)bis(methylcyclohexane) in the distillation bottoms;

(vi). separating the upper and lower layers of step (v) and recovering the 1,3-cyclohexanedimethanol from the lower layer by distillation; and (vii). recycling at least a portion of the (3-methylcyclohexyl)methanol from step (iv) to step (i).

DETAILED DESCRIPTION

The present invention provides a process for the preparation of 1,3-cyclohexanedimethanol by esterifying isophthalic acid (abbreviated herein as "IPA") with (3-methylcyclohexyl)methanol ("3-MCHM") and hydrogenating this ester to 1,3-CHDM. In a general embodiment, the invention provides a process for the preparation of 1,3-cyclohexanedimethanol from isophthalic acid comprising:

(i). contacting isophthalic acid and (3-methylcyclohexyl)methanol in a reaction zone at a temperature of about 150° C. to about 280° C. while removing water from the reaction zone, to form an esterification product mixture comprising bis(3-methylcyclohexyl)methyl)isophthalate, (ii). contacting the esterification product mixture with hydrogen in a first hydrogenation zone in the presence of a catalyst effective for hydrogenation of an aromatic ring to produce a liquid effluent comprising bis(3-methylcyclohexyl)methyl)cyclohexane-1,3-dicarboxylate;

(iii). contacting the effluent from the first hydrogenation zone with hydrogen in the presence of an ester hydrogenation catalyst in a second hydrogenation zone to produce a hydrogenation product comprising 1,3-cyclohexanedimethanol, 3,3'-oxybis(methylene)bis(methylcyclohexane), and (3-methylcyclohexyl)methanol, and;

(iv). recycling at least a portion of the (3-methylcyclohexyl)methanol from step (iii) to step (i).

The 3-MCHM used as a starting material for our process is produced as a by-product in the production of 1,3-cyclohexanedimethanol. Thus, because the esterification process does not introduce any new materials (e.g., methanol to make dimethyl isophthalate) into the overall 1,3-CHDM process, our novel process reduces the amount equipment needed for the preparation of 1,3-cyclohexanedimethanol from isophthalic acid and simplifies the purification of the final product.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, each numerical parameter should at least be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.1113, etc., and the endpoints 0 and 10. Also, a range associated with chemical substituent groups such as, for example, "C1 to C5 hydrocarbons," is intended to specifically include and disclose C1 and C5 hydrocarbons as well as C2, C3, and C4 hydrocarbons.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

As used in the specification and the claims, the singular forms "a," "an" and "the" include their plural referents unless the context clearly dictates otherwise. For example, reference to a "promoter" or a "reactor" is intended to include the one or more promoters or reactors. References to a composition or process containing or including "an" ingredient or "a" step is intended to include other ingredients or other steps, respectively, in addition to the one named.

The terms "containing" or "including," are synonymous with the term "comprising," and is intended to mean that at least the named compound, element, particle, or method step, etc., is present in the composition or article or method, but does not exclude the presence of other compounds, catalysts, materials, particles, method steps, etc., even if the other such compounds, material, particles, method steps, etc., have the same function as what is named, unless expressly excluded in the claims.

It is also to be understood that the mention of one or more method steps does not preclude the presence of additional method steps before or after the combined recited steps or intervening method steps between those steps expressly identified. Moreover, the lettering of process steps or ingredients is a convenient means for identifying discrete activities or ingredients and the recited lettering can be arranged in any sequence, unless otherwise indicated.

The esterification step of our process comprises contacting isophthalic acid with 3-MCHM in a reaction zone, under elevated temperatures, and removing the water produced in the esterification from the reaction zone as the reaction progresses. The molar ratio of alcohol to acid that can be used is typically at least 2:1. For example, the ratio of 3-MCHM to isophthalic acid can be about 2:1 to about 10:1. Some additional examples of molar ratios of alcohol to acid in the esterification step include about 2:1 to about 9:1; about 2:1 to about 8:1; about 2:1 to about 7:1; about 2:1 to about 5:1; about 2:1 to about 4:1; and about 2:1 to about 3:1.

It is advantageous to remove the water produced by the esterification reaction in order to improve the rate of the reaction and the conversion to the isophthalic acid diester. Removal of the water may be accomplished by any conventional means known to persons skilled in the art such as, for example, by distillation, membrane separation, the use of absorbents, or combinations thereof. For example, the water of reaction may be removed by simple distillation from the esterification reaction or by azeotropic distillation with 3-MCHM. With azeotropic distillation, the 3-MCHM/water azeotrope is allowed to separate into a 3-MCHM layer and a water layer, the water layer removed, and the 3-MCHM layer returned to the esterification reaction. In another example, the water of the reaction can be removed by azeotropic distillation by adding a solvent to the esterification reaction mixture that forms an azeotrope with water under the esterification conditions of temperature and pressure. The use of azeotropic solvents, however, will, in general, require additional steps to remove the azeotropic solvent from either the esterification or 1,3-CHDM reaction product mixture. The water of reaction may also be removed by exposing or passing the reaction mixture through an adsorbent. The removal of the water of reaction from the reaction zone also may be assisted by passing an inert gas through the IPA-3-MCHM reaction mixture in the reaction zone and condensing the water from the inert gas stream after it exits the reactor. Nitrogen is an example of an appropriate inert gas. The inert gas typically is fed below the surface of the IPA-3-MCHM reaction mixture by means of a conventional conduit or via a gas sparging device. The inert gas may be fed intermittently or discontinuously. For example, the inert gas can be fed continuously at the commencement of the esterification reaction. The amount of gas passed through the IPA-3-MCHM reaction mixture may vary significantly but typically is in the range of about 2 to 5 volumes of gas per volume of reaction mixture per hour. It will be apparent to persons skilled in the art that numerous variations and combinations of these methods are possible.

The esterification may be carried out by the joint addition of the IPA and 3-MCHM or by the incremental addition of one of the feed substrate materials to the other. For example, the isophthalic acid can be added incrementally to a reaction zone that contains the full amount of the alcohol to be used in the esterification reaction. Alternatively, the 3-MCHM may be added incrementally to the full or partial amount of IPA that is to be used in the esterification process. The term "incrementally," as used herein, is intended to have its plain meaning of adding the IPA component or 3-MCHM component to the reaction zone in one or more increments or portions to increase the amount of the 3-MCHM or IPA component in the reaction zone. The increments do not have to be equal in size. For example, one increment may contain 90% of the total amount of IPA component and a second increment may contain the remaining 10%. The increments may be added stepwise in discrete portions, continuously, or in a combination thereof. Therefore, the term "incrementally," as used in the description and claims, is intended to include both continuous and stepwise additions of the 3-MCHM and/or IPA components. Thus, "incrementally" means that, over the duration of the entire process, the 3-MCHM or IPA components can be added to the reaction zone continuously, stepwise in 2 or more stages or discrete steps, or in a combination of continuous and stepwise addition. Thus, in one embodiment of the invention, the IPA component is added to the reaction zone in 2 or more stages. In another embodiment, the IPA component is added to the reaction zone continuously.

The IPA and 3-MCHM are contacted in a reaction zone at a temperature of about 150 to about 280° C. under atmospheric or super atmospheric pressures as needed to maintain a liquid reaction mixture. For example, the IPA and 3-MCHM can be contacted at a temperature of about 190 to about 230° C. at pressures of up to about 50 bar gauge. Additional examples of temperature ranges are about 150 to about 300° C., about 180 to about 280° C., and about 190 to about 250° C.

The IPA and 3-MCHM are reacted while removing water from the reaction mixture to form an esterification product mixture comprising bis(3-methylcyclohexyl)methyl)isophthalate, represented by formula (I), and unreacted (3-methylcyclohexyl)methanol. In one embodiment of the process, the IPA and 3-MCHM are heated together with water removal until a product mixture having a desired conversion is obtained.

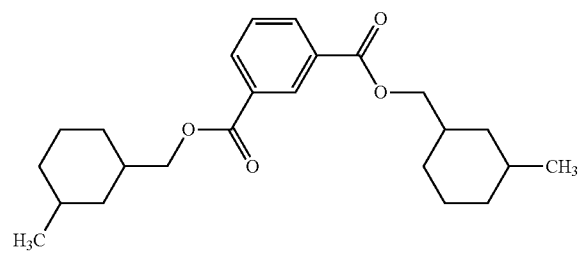

(I)

The desired conversion can be determined by conventional analytical methods known to persons skilled in the art such as, for example, by NMR, titration (i.e., acid number), gas chromatography, and liquid chromatography. Acid number may be determined by titration of the esterification product mixture with potassium hydroxide and is reported as mg of potassium hydroxide consumed for each gram of esterification product mixture (mg KOH/g esterification product mixture). The esterification product mixture will typically have an acid number of about 10 mg KOH or less/gram of esterification product mixture to reduce poisoning and deactivation of any hydrogenation catalysts in the subsequent steps of the process. Additional examples of acid number values for the esterification product mixture are about 8 mg KOH or less/gram of esterification product mixture, about 5 mg KOH or less, and about 3 mg KOH or less. The esterification step may also be monitored by measuring the water evolved from the reaction mixture, computer modeling of the reaction rate, or any other means capable of determining the concentration of reactants or products in the esterification product mixture.

The 3-MCHM used to esterify IPA in the process of the invention is produced as a by-product in the production of 1,3-CHDM by the multistage hydrogenation of IPA diesters that proceeds by hydrogenation of the aromatic ring produce the corresponding 1,3-cyclohexanedicarboxylate diester, which is further hydrogenated to produce 1,3-CHDM. In one embodiment of our invention, therefore, the 3-MCHM used in the esterification reaction with IPA can be recovered and recycled from a process for the preparation of 1,3-CHDM by hydrogenation of bis(3-methylcyclohexyl)methyl)isophthalate. The 3-MCHM used in the esterification may also include unreacted 3-MCHM that has been recovered and recycled from the esterification step of our 1,3-CHDM process. In one embodiment of our invention, the 3-MCHM used to esterify IPA, recycled to the esterification step, or a combination thereof, further comprises one or more additional alcohols having 4 to 20 carbon atoms in minor or major quantities. In another embodiment, the one or more additional alcohols comprise 1-butanol, 2-butanol, 2-ethylhexanol, cyclohexanol, benzyl alcohol, 1-hexanol, 1-pentanol, 1-octanol, 1-nonanol, 1-decanol, or combinations thereof. In yet another embodiment, the 3-MCHM used to esterify IPA in step (i) contains from 0 to than 5 weight percent of the one or more additional alcohols based on the total amount of 3-MCHM used in the esterification step. Some other examples of the concentration of the additional alcohols are 0 to less than 3 weight percent, 0 to less than 2 weight percent, 0 to less than 1 weight percent, and 0 to less than 0.5 weight percent.

The esterification reaction may be carried out in the presence or absence of an exogenous esterification catalyst, i.e., a catalyst other than isophthalic acid, that is added to the reaction mixture for the purpose of increasing the rate of the esterification reaction. Any esterification catalyst that is known in art may be used. For example, the IPA and 3-MCHM can be contacted in the presence of a catalyst comprising compounds of titanium, magnesium, aluminum, boron, silicon, tin, zirconium, zinc, antimony, manganese, calcium, vanadium, sulfuric acid, p-toluene sulfonic acid, methane sulfonic acid, or phosphoric acid. For example, acetates, chlorides, nitrates, sulfates, oxides and alkoxides of metals such as zinc, manganese, tin, titanium, antimony, cobalt and lithium may be used. Buffering compounds, such as alkaline salts of organic acids, can be included with the catalysts if desired.

Some representative examples of catalysts that may be used in the esterification step include, but are not limited to, titanium, zirconium, and tin alcoholates, carboxylates, and chelates; zinc acetate; zinc oxide, antimony oxide, stannous oxalate, zinc acetyl acetonate, calcium oxide, and manganese oxide. Titanium and zirconium catalysts are frequently used for esterification of isophthalic acid. Some typical titanium alcoholates which can be used as catalysts include tetramethyl titanates, tetraethyl titanates, tetrapropyl titanates, tetraisopropyl titanates, tetrabutyl titanates, tetrapentyl titanates, tetrahexyl titanates, and tetraoctyl titanates. The alkoxy groups on the titanium atom can all be the same or they can be different. The zirconium counterparts of the above alcoholates can be substituted in whole or in part as catalysts. Typically, the concentration of catalyst can be about 0.03 to about 1 weight percent, based on total weight of esterification reaction mixture.

Although the esterification process may be carried out in the presence of a catalyst, we have found that IPA has a high solubility at esterification temperatures in 3-MCHM, which allows the esterification reaction to proceed smoothly without added catalysts. Thus, in one embodiment of the invention, the IPA and 3-MCHM are contacted in the absence of an exogenous catalyst. Conducting the esterification reaction step in the absence of a catalyst avoids the need for additional purification steps to remove catalyst residues which can poison the hydrogenation catalysts or catalyze the formation of color bodies and other undesirable by-products in the subsequent steps of the instant process.

The process of the present invention may be carried out in a batch, semi-continuous or continuous mode. In the batch mode, for example, an agitated pressure vessel may be charged with IPA and 3-MCHM, heated and pressurized and the esterification is carried out under reflux conditions while removing water from the reaction mixture. The high solubility of IPA in 3-MCHM, as noted above, also allows the esterification to be conducted in a continuous mode with lower residence times and smaller reactors than would be typically used for the esterification of IPA with other alcohols. Any alcohol that is removed from the reaction mixture with the water can be recovered and fed back to the reaction vessel over the course of the process. At the conclusion of the reaction, the esterification product mixture can be used in the subsequent hydrogenation step as is or the unreacted 3-MCHM may recovered from esterification product mixture by distillation or any conventional means known to persons skilled in the art and recycled. Continuous operation involves continuously or intermittently feeding IPA and 3-MCHM to and continuously or intermittently removing alcohol, water and product-containing reaction mixture from a vessel maintained at a predetermined temperature, pressure and liquid level. It will be apparent to those skilled in the art that other reactor schemes may be used with this invention. For example, the esterification reaction can be conducted in a plurality of reaction zones, in series, in parallel, or it may be conducted batch wise or continuously in a tubular plug flow reaction zone or series of such zones with recycle of unconsumed feed substrate materials if required. For example, the esterification reaction mixture may be fed to one or more secondary reaction vessels wherein conversion of IPA and/or IPA half-ester to the diester product is completed.

The esterification product mixture typically can comprise at least 50 weight percent of bis(3-methylcyclohexyl)methyl) isophthalate based on the total weight of the esterification product mixture, although lower concentrations may be present. Other examples of weigh percentages of bis(3-methylcyclohexyl)methyl)isophthalate in the esterification product mixture are at least 60 weight percent, at least 70 weight percent, at least 80 weight percent, and at least 90 weight percent.

The esterification product mixture can be contacted with hydrogen in a first hydrogenation zone in the presence of a catalyst effective for hydrogenation of an aromatic ring to produce a liquid effluent that comprises bis(3-methylcyclohexyl)methyl)cyclohexane-1,3-dicarboxylate, represented by formula (II):

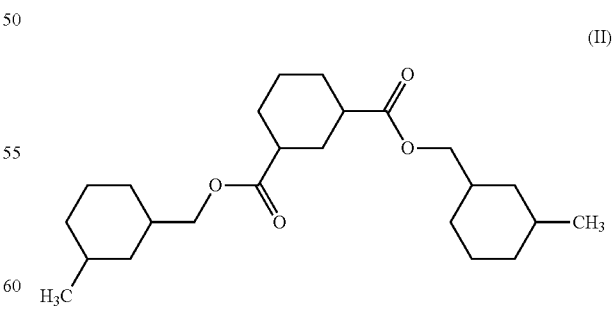

The hydrogenation of the esterification product mixture may be carried out over a temperature range of about 150° to 350° C. Generally, higher temperatures favor carbon monoxide formation and, therefore, the use of temperatures in the upper part of the range may require means for removing carbon monoxide from the hydrogenation zone such as, for example, by purging all, or substantially all, of the hydrogen effluent of the process. Other examples of temperatures for the hydrogenation of the esterification product mixture include about 160 to about 300° C., about 180 to about 300° C., about 170 to about 280° C., about 170 to about 260° C., and about 170° C. to about 240° C. The process may be operated in either an adiabatic or isothermal process.

The hydrogenation of the esterification product mixture may be performed within a pressure range of about 50 to 400 bar gauge. In another example, the pressure of the hydrogenation may range from about 50 to about 170 bar gauge.

The hydrogenation of the esterification product mixture can be carried out in a batch, semi-continuous or continuous mode using conventional chemical processing techniques. In another embodiment of the present invention, the process comprises a combination of two or more of batch, semi-continuous or continuous modes. In certain embodiments, the mode of operation may be a continuous process in which the esterification product mixture is passed over and through one or more fixed beds of catalyst in a "trickle bed" manner and all or a portion of the bis(3-methylcyclohexyl)-methyl) isophthalate is converted to bis(3-methylcyclohexyl)methyl)cyclohexane-1,3-dicarboxylate (II). For example, a portion of the effluent from one or more fixed catalyst beds, comprising bis(3-methylcyclohexyl)methyl)cyclohexane-1,3-dicarboxylate (II) may be recycled to the feed port of the reactor where it serves as a solvent for the esterification product feed. In another embodiment, the esterification product mixture may be supplied to the hydrogenation zone at a rate which will result in substantially complete conversion of the reactant to the cyclohexanedicarboxylate product. In some embodiments of the present invention, one or more inert, non-aromatic compounds, which are liquid under the operating conditions employed, may be used as a solvent or solvent mixture. Examples of suitable solvents include, but not limited to, alcohols, such as 3-MCHM and 1,3-CHDM, and other esters.

The most suitable LHSV (LHSV, liquid hourly space velocity, is the unit volume of reactant fed per hour per unit volume catalyst) for the esterification product mixture feed is dependent upon the particular temperature and pressure used which, as mentioned hereinabove, can depend upon the flow rate and/or purity of the hydrogen. In trickle bed operation, the liquid hourly space velocity of the esterification product mixture feed may be in the range of about 0.1 to 10 with a preferred range of 0.5 to 5. In some embodiments the lower limit of the LHSV of the esterification product mixture feed may be 0.1 or 0.2 or 0.3 or 0.4 or 0.5 or 0.6 or 0.7 or 0.8 or 0.9 or 1.0 or 2.0 or 3.0 or 4.0 or 5.0 or 6.0 or 7.0 or 8.0 or 9.0. In some embodiments the upper limit of the LHSV of the esterification product mixture feed may be 0.2 or 0.3 or 0.4 or 0.5 or 0.6 or 0.7 or 0.8 or 0.9 or 1.0 or 2.0 or 3.0 or 4.0 or 5.0 or 6.0 or 7.0 or 8.0 or 9.0 or 10.0. The range of the LHSV of the esterification product mixture feed may be a combination of any lower limit with any upper limit listed above.

The LHSV for the total liquid flow (esterification product mixture feed plus solvent) may be in the range of 1 to 40. In some embodiments, the lower limit of the LHSV of the total liquid flow may be 1.0 or 2.0 or 3.0 or 4.0 or 5.0 or 6.0 or 7.0 or 8.0 or 9.0 or 10 or 15 or 20 or 25 or 30 or 35. In some embodiments the upper limit of the LHSV of the total liquid flow may be 2.0 or 3.0 or 4.0 or 5.0 or 6.0 or 7.0 or 8.0 or 9.0 or 10 or 15 or 20 or 25 or 30 or 35 or 40. The range of the LHSV of the total liquid flow may be a combination of any lower limit with any upper limit listed above.

The hydrogen gas used in the process may comprise fresh gas or a mixture of fresh gas and recycle gas. The hydrogen gas can be a mixture of hydrogen, optional minor amounts of components such as CO and $CO_2$, and inert gases, such as argon, nitrogen, or methane, containing at least about 70 mole % of hydrogen. For example, the hydrogen gas can contain at least 90 mole % or, in another example, at least 97 mole %, of hydrogen. The hydrogen gas may be obtained from any of the common sources well known in the art such as, for example, by partial oxidation or steam reforming of natural gas. Pressure swing absorption can be used if a high purity hydrogen gas is desired. If gas recycle is utilized in the process, then the recycle gas will normally contain minor amounts of one or more products of the hydrogenation reaction which have not been fully condensed in the product recovery stage downstream from the hydrogenation zone. Thus, when using gas recycle in the process of the invention, the gas recycle stream will typically contain a minor amount of an alkanol, e.g., 3-MCHM. Hydrogen is typically fed to the reactor in excess of the stoichiometric quantity and normally is purged from the system. The rate of hydrogen purge is dependent on the temperature and pressure at which the process is operated.

The hydrogenation of the esterification product mixture may be catalyzed by any catalyst that is effective for the reduction of an aromatic ring. In certain embodiments for example, the catalyst can comprise a Group VIII metal (Groups 8, 9, and 10 according to IUPAC numbering) deposited on a catalyst support material comprising alumina, silica-alumina, titania, zirconia, chromium oxides, graphite, silicon carbide, or combinations thereof. Examples of the Group VIII metals that may be used include, but are not limited to, palladium, platinum, ruthenium, nickel and combinations thereof. In one embodiment of the present invention the total amount of Group VIII metal present may be about 0.1 to 10 weight percent based on the total weight of the catalyst. The lower limit of the weight percent of the Group VIII metal may be 0.1 or 0.2 or 0.3 or 04 or 0.5 or 0.6 or 0.7 or 0.8 or 0.9 or 1.0 or 2.0 or 3.0 or 4.0 or 5.0 or 6.0 or 7.0 or 8.0 or 9.0. The upper limit of the weight percent of the Group VIII metal may be 0.2 or 0.3 or 04 or 0.5 or 0.6 or 0.7 or 0.8 or 0.9 or 1.0 or 2.0 or 3.0 or 4.0 or 5.0 or 6.0 or 7.0 or 8.0 or 9.0 or 10.0. The range of the weight percent of the Group VIII metal may be any combination of any lower limit with any upper limit. For example, the catalyst can comprise palladium supported on alumina. In another embodiment of the present invention the catalyst can comprise about 0.5 to 5 weight percent palladium wherein the weight percentages are based on the total weight of the catalyst, e.g., the total weight of the support material plus the Group VIII metal. In another embodiment of the present invention the catalysts further comprise about 0.5 to 5 weight percent palladium, optionally in combination with about 0.01 to 2 weight percent nickel, ruthenium or a mixture thereof, wherein the weight percentages are based on the total weight of the catalyst, e.g., the total weight of the support material plus the metals. The catalyst may be in any conventional form such as, for example, in the form of extrudates, granules, and pellets for use in fixed-bed reactor processes and powder for slurry processes. The shape of the supports may be, but are not limit to, cylinders, spheres, stars or any type of multiple-lobe shapes. Depending on the particular support material employed and/or the method used to prepare a catalyst, the Group VIII metal may be deposited primarily on the surface of the support or distributed substantially throughout the support.

The catalysts may be prepared by conventional techniques such as impregnation of one or more Group VIII metals or Group VIII metal compounds on or into the support material.

The Group VIII metals may be provided as zero valence metals or as oxidized metals in the form of compounds such as salts of inorganic or organic acids and organometallic complexes. In one embodiment, the support materials may be impregnated with one or more Group VIII metals by immersing the support material in a solution of a Group VIII metal compound in a suitable solvent such as water or an organic solvent. The support material then is dried and the metal compound is reduced to a Group VIII metal.

In one example of the invention, the esterification product mixture may be contacted with hydrogen at a temperature of about 150 to about 350° C. and a pressure of about 50 to about 400 bar gauge and in the presence of a catalyst comprising palladium, platinum, nickel, ruthenium or combinations thereof deposited on a catalyst support material. In another embodiment, the esterification product mixture is contacted with hydrogen at a temperature of about 180 to about 300° C. and a pressure of about 50 to about 170 bar gauge, in the presence of a catalyst comprising palladium, ruthenium, or combinations thereof, deposited on a catalyst support material comprising alumina, silica-alumina, titania, zirconia, chromium oxides, graphite, silicon carbide, or combinations thereof. It will be apparent to persons skilled in the art that other combinations of temperature, pressure, and catalysts may be used.

The hydrogenation of the esterification product mixture in the first hydrogenation zone produces a liquid effluent comprising bis(3-methylcyclohexyl)-methyl)cyclohexane-1,3-dicarboxylate and, optionally, (3-methylcylohexyl)methanol. The liquid effluent is contacted with hydrogen in the presence of an ester hydrogenation catalyst in a second hydrogenation zone to produce a hydrogenation product comprising 1,3-cyclohexanedimethanol, 3,3'-oxybis(methylene)bis(methylcyclohexane), represented by formula (III) and abbreviated to hereinafter as "3-MCHM-diether," and (3-methylcyclohexyl) methanol. The 3-MCHM can comprise 3-MCHM that was present in the esterification product mixture, released during the hydrogenation of the

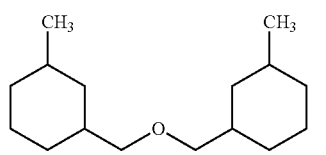

III bis(3-methylcyclohexyl)methyl)cyclohexane-1,3-dicarboxylate, and additionally produced as a by-product.

The hydrogenation conditions of pressure and temperature for the liquid effluent from the first hydrogenation zone may be varied depending not only on one another but also on the activity of the catalyst, the mode of operation, selectivity considerations, and the desired rate of conversion. The process typically is conducted at temperatures in the range of about 160° C. to about 300° C. and pressures in the range of about 40 to about 400 bar gauge (abbreviated herein as "barg"). Further examples of temperatures and pressures at which the process of the invention may be operated are about 175 to about 300° C. at about 200 to about 380 barg, and about 200 to about 250° C. at about 300 to about 350 barg. While rates and conversions generally also increase with increasing pressure, the energy costs for compression of hydrogen, as well as the increased cost of high-pressure equipment generally make the use of the lowest pressure practical advantageous.

The process of this invention may be carried out in the absence or presence of an inert solvent, i.e., a solvent for the cyclohexanedicarboxylate ester being hydrogenated which does not affect significantly the activity of the catalyst and does not react with the hydrogenation product or products. Examples of such solvents include alcohols such as ethanol and lauryl alcohol; glycols such as mono-, di- and tri-ethylene glycol; hydrocarbons such as hexane, cyclohexane, octane and decane; and aromatic ethers such as diphenyl ether, etc. It is often economically advantageous, however, to conduct the process in the absence of solvent and use the neat, molten cyclohexanedicarboxylate ester alone or as a mixture with 1,3-cyclohexanedimethanol and other hydrogenation products as the feed to the process.

The hydrogenation of the liquid effluent containing the cyclohexanedicarboxylate ester (II) may be carried out as a batch, semi-continuous or continuous process and may utilize a variety of reactor types. Examples of suitable reactor types include, but are not limited to, stirred tank, continuous stirred tank, slurry, tubular, fixed bed, and trickle bed. A plurality of reactors, stages, or hydrogenation zones may be used. For economic and operability reasons, the process is advantageously operated as a continuous process. Continuous operation may utilize a fixed bed with a larger particle size of catalyst such as, for example, granules, pellets, various multilobal shaped pellets, rings, or saddles that are well known to skilled persons in the art. As an example of a continuous process, the catalyst bed may be fixed in a high pressure, tubular or columnar reactor and the liquid effluent from the first hydrogenation zone, dissolved in an inert solvent if necessary or desired, fed continuously into the top of the bed at elevated pressure and temperature, and the crude hydrogenation product removed from the base of the reactor. Alternatively, it is possible to feed the liquid effluent containing the cyclohexanedicarboxylate ester (II) into the bottom of the bed and remove the crude product from the top of the reactor. It is also possible to use 2 or more catalyst beds or hydrogenation zones connected in parallel or in series to improve conversion, to reduce the quantity of catalyst, or to bypass a catalyst bed for periodic maintenance or catalyst removal. Another mode of continuous operation utilizes a slurry of the catalyst in an agitated pressure vessel which is equipped with a filter leg to permit continuous removal of a solution of product in unreacted ester and/or an inert solvent. In this manner a liquid reactant or reactant solution can be continuously fed to and product solution continuously removed from an agitated pressure vessel containing an agitated slurry of the catalyst.

In one example, a portion of the hydrogenation product from one or more fixed catalyst beds, comprising 1,3-CHDM may be recycled to the feed port of the reactor where it serves as a solvent for the liquid effluent feed containing the cyclohexanedicarboxylate ester (II). In another embodiment, the liquid effluent feed may be supplied to the hydrogenation zone at a rate which will result in substantially complete conversion of the cyclohexanedicarboxylate ester (II) to the 1,3-CHDM product. In some embodiments of the present invention, one or more inert, non-aromatic compounds, which are liquid under the operating conditions employed, may be used as a solvent or solvent mixture. Examples of suitable solvents include, but not limited to, alcohols, such as 3-MCHM and 1,3-CHDM, and other esters.

The process may be conducted in the liquid phase, the vapor phase, or as combination of the liquid and vapor phase. For example, the process may be carried in the vapor phase as described, for example, in U.S. Pat. No. 5,395,987. In one example of a vapor phase operation, the process of the invention may be operated using vaporous feed conditions by feeding the liquid effluent containing the cyclohexanedicarboxylate ester (II) to a hydrogenation zone comprising the ester hydrogenation catalyst in essentially liquid free vaporous form. Hence, the feed stream is introduced into the hydrogenation zone at a temperature which is above the dew point of the mixture. The process may be operated so that vapor phase conditions will exist throughout the hydrogenation zone. Such a vapor phase process often has the advantage of lower operating pressures in comparison to liquid phase process which can reduce the construction and operating costs of a commercial plant.

The most suitable LHSV for the liquid effluent feed from the first hydrogenation zone is dependent upon the particular temperature and pressure used which, as mentioned hereinabove, can depend upon the flow rate and/or purity of the hydrogen. In trickle bed operation, the liquid hourly space velocity of the liquid effluent feed may be in the range of about 0.1 to 10 with a preferred range of 0.5 to 5. In some embodiments the lower limit of the LHSV of the liquid effluent feed may be 0.1 or 0.2 or 0.3 or 0.4 or 0.5 or 0.6 or 0.7 or 0.8 or 0.9 or 1.0 or 2.0 or 3.0 or 4.0 or 5.0 or 6.0 or 7.0 or 8.0 or 9.0. In some embodiments the upper limit of the LHSV of the liquid effluent feed may be 0.2 or 0.3 or 0.4 or 0.5 or 0.6 or 0.7 or 0.8 or 0.9 or 1.0 or 2.0 or 3.0 or 4.0 or 5.0 or 6.0 or 7.0 or 8.0 or 9.0 or 10.0. The range of the LHSV of the liquid effluent feed may be a combination of any lower limit with any upper limit listed above.

The LHSV for the total liquid flow (liquid effluent feed plus solvent) may be in the range of 1 to 40. In some embodiments the lower limit of the LHSV of the total liquid flow may be 1.0 or 2.0 or 3.0 or 4.0 or 5.0 or 6.0 or 7.0 or 8.0 or 9.0 or 10 or 15 or 20 or 25 or 30 or 35. In some embodiments the upper limit of the LHSV of the total liquid flow may be 2.0 or 3.0 or 4.0 or 5.0 or 6.0 or 7.0 or 8.0 or 9.0 or 10 or 15 or 20 or 25 or 30 or 35 or 40. The range of the LHSV of the total liquid flow may be a combination of any lower limit with any upper limit listed above.

The hydrogen gas used in the process may comprise fresh gas or a mixture of fresh gas and recycle gas. The hydrogen gas can be a mixture of hydrogen, optional minor amounts of components such as CO and $CO_2$, and inert gases, such as argon, nitrogen, or methane, containing at least about 70 mole % of hydrogen. For example, the hydrogen gas contains at least 90 mole % or, in another example, at least 97 mole %, of hydrogen. The hydrogen gas may be obtained from any of the common sources well known in the art such as, for example, by partial oxidation or steam reforming of natural gas. Pressure swing absorption can be used if a high purity hydrogen gas is desired. If gas recycle is utilized in the process, then the recycle gas will normally contain minor amounts of one or more products of the hydrogenation reaction which have not been fully condensed in the product recovery stage downstream from the hydrogenation zone. Thus, when using gas recycle in the process of the invention, the gas recycle stream will typically contain a minor amount of an alkanol, e.g., 3-MCHM. Hydrogen is typically fed to the reactor in excess of the stoichiometric quantity and normally is purged from the system. The rate of hydrogen purge is dependent on the temperature and pressure at which the process is operated.

The hydrogenation of the cyclohexanedicarboxylate ester (II) in the liquid effluent from the first hydrogenation zone may be catalyzed by any catalyst that is effective for the reduction of esters to alcohols. Typical ester hydrogenation catalysts include copper-containing catalysts and Group VIII metal-containing catalysts. Examples of suitable copper-containing catalysts include copper-on-alumina catalysts, copper oxide, reduced copper oxide/zinc oxide catalysts, with or without a promoter, manganese promoted copper catalysts, and reduced copper chromite catalysts, with or without a promoter, while suitable Group VIII (Groups 8, 9, and 10 according to IUPAC numbering) metal-containing catalysts include platinum, palladium, nickel, and cobalt catalysts. Suitable copper oxide/zinc oxide catalyst precursors include CuO/ZnO mixtures wherein the Cu:Zn weight ratio ranges from about 0.4:1 to about 2:1. Promoted copper oxide/zinc oxide precursors include CuO/ZnO mixtures wherein the Cu:Zn weight ratio ranges from about 0.4:1 to about 2:1 which are promoted with from about 0.1% by weight up to about 15% by weight of barium, manganese or a mixture of barium and manganese. Such promoted CuO/ZnO mixtures include the Mn-promoted CuO/ZnO precursor. Suitable copper chromite catalyst precursors include those wherein the Cu:Cr weight ratio ranges from about 0.1:1 to about 4:1, preferably from about 0.5:1 to about 4:1. Promoted copper chromite precursors include copper chromite precursors wherein the Cu:Cr weight ratio ranges from about 0.1:1 to about 4:1, preferably from about 0.5:1 to about 4:1, which are promoted with from about 0.1% by weight up to about 15% by weight of barium, manganese or a mixture of barium and manganese. Manganese promoted copper catalyst precursors typically have a Cu:Mn weight ratio of from about 2:1 to about 10:1 and can include an alumina support, in which case the Cu:Al weight ratio is typically from about 2:1 to about 4:1. In certain embodiments for example, the catalyst can comprise a Group VIII metal deposited on a catalyst support material comprising alumina, silica-alumina, titania, zirconia, chromium oxides, graphite, silicon carbide, or combinations thereof.

The ester hydrogenation catalyst may also comprise Raney metal catalysts. The Raney metal catalyst may comprise any catalytically active metal useful for the hydrogenation of cyclohexanedicarboxylate esters to the corresponding cyclohexanedimethanols. Exemplary Raney metals include nickel, cobalt, copper, or combinations thereof. For example, the Raney metal catalyst may comprise nickel. The term "Raney metal," as used herein, means a metal produced by the "Raney" process, that is, a process in which the metal catalyst is prepared by selective removal of one or more components from an alloy and leaving the remaining metal behind as the catalyst. The Raney process is described, for example, in U.S. Pat. Nos. 1,628,190 and 6,284,703. The alloy components may be removed by any method, e.g., dissolving out by chemical means or by volatilization, etc. Typically, the Raney metal is produced by contacting an alloy of the metal, containing leachable alloying components such as aluminum, zinc, silicon, or a combination thereof, with sodium hydroxide. The catalytic metal that remains is generally in a highly active porous or finely divided state. The ratio by weight of Raney process metal to leachable alloying component in the catalyst alloy may be in the range of about 10:90 to about 90:10, as is normally the case with Raney alloys. The Raney catalyst may also comprise a metal binder which does not have to be the same as the catalytically active metal present in the catalyst alloy. Rather, it is possible to combine different Raney process metals with each other as well as with promoter metals, in the catalyst alloy and as binder, offering a further degree of freedom when adjusting the catalytic properties to the particular catalytic process. For example, the binder can be nickel, cobalt, copper, iron and, optionally, promoter metals. Generally any of the metals used for making Raney metal catalysts are suitable. The binder metal may be employed in an unreachable and unadulterated form.

In one embodiment of the process of the invention, the liquid effluent from the first hydrogenation zone is contacted with hydrogen at a temperature of 160 to about 300° C. at a pressure of about 40 to about 400 bar gauge in the presence of an ester hydrogenation catalyst comprising at least one Group VIII metal, a copper-containing catalyst, or a combination thereof. In another embodiment, the ester hydrogenation catalyst comprises copper chromite, copper oxide, Raney nickel, Raney cobalt, or combinations thereof, and is optionally promoted with zinc, barium, calcium, manganese, magnesium, nickel, ruthenium, or lanthanum. Other possible combinations of temperatures, pressures, and catalysts will be apparent to persons having ordinary skill in the art.

The hydrogenation of the effluent from the first hydrogenation zone produces a hydrogenation product comprising 1,3-cyclohexanedimethanol, 3,3'-oxybis(methylene)bis(methylcyclohexane) (III), and (3-methylcyclohexyl)methanol that was present in the esterification product mixture, released during the hydrogenation of the bis(3-methylcyclohexyl)methyl)cyclohexane-1,3-dicarboxylate, and additionally produced as a by-product. The 3-MCHM that is present in the hydrogenation product comprises unreacted 3-MCHM that was present in and carried forth with the esterification product mixture and 3-MCHM that is released by the hydrogenation of bis(3-methylcyclohexyl)methyl)cyclohexane-1,3-dicarboxylate (II). It will apparent to persons skilled in the art that the hydrogenation of 1 mole of cyclohexanedicarboxylate ester (II) will produce 2 moles of 3-MCHM and 1 mole of 1,3-CHDM. Additional 3-MCHM is produced as a by-product of the overall hydrogenation of bis(3-methylcyclohexyl)methyl)isophthalate to 1,3-CHDM. Thus, the term "by-product," as used herein in reference to the 3-MCHM present in the hydrogenation products of the present invention, is understood to mean the 3-MCHM that is additionally produced in the first and second hydrogenation zones and is present in addition to the unreacted 3-MCHM present in esterification product mixture and the 3-MCHM released by the hydrogenation of the cyclohexanedicarboxylate ester (II).

The 3-MCHM in the hydrogenation product from the second hydrogenation zone can be recovered and recycled to the esterification step with isophthalic acid. For example, the 3-MCHM in the hydrogenation product can be recovered by distillation of the hydrogenation product mixture. Fractional distillation may be employed to improve the separation of the various components of the hydrogenation product. The recovered and/or recycled 3-MCHM may further comprise one or more additional alcohols having 4 to 20 carbon atoms in minor or major quantities. Some representative examples of additional alcohols that may be present in the recycled 3-MCHM are 1-butanol, 2-butanol, 2-ethylhexanol, cyclohexanol, benzyl alcohol, 1-hexanol, 1-pentanol, 1-octanol, 1-nonanol, 1-decanol, or combinations thereof.

Another embodiment of our invention is a process for the preparation of 1,3-cyclohexanedimethanol from isophthalic acid, comprising:

(i). contacting isophthalic acid and (3-methylcyclohexyl)methanol in a mole ratio of alcohol to acid of about 2:1 to about 5:1, in a reaction zone at a temperature of about 150° C. to about 280° C. in the absence of a exogenous catalyst, while removing water from the reaction zone, to form an esterification product mixture comprising bis(3-methylcyclohexyl)methyl)isophthalate and unreacted (3-methylcyclohexyl)methanol;

(ii). contacting the esterification product mixture with hydrogen in a first hydrogenation zone in the presence of a palladium on alumina catalyst to produce a liquid effluent comprising bis(3-methylcyclohexyl)methyl)cyclohexane-1,3-dicarboxylate;

(iii). contacting the effluent from the first hydrogenation zone with hydrogen in the presence of a copper chromite catalyst in a second hydrogenation zone to produce a hydrogenation product comprising 1,3-cyclohexanedimethanol, 3,3'-oxybis(methylene)bis(methylcyclohexane), and (3-methylcyclohexyl)methanol;

(iv). recovering the (3-methylcyclohexyl)methanol from the hydrogenation product by distillation; and (v). recycling at least a portion of the (3-methylcyclohexyl)methanol to step (i).

For example, the hydrogenation of the effluent from the first hydrogenation zone produces a hydrogenation product comprising 1,3-cyclohexanedimethanol, 3,3'-oxybis(methylene)bis(methylcyclohexane) (III), and (3-methylcyclohexyl)methanol that was present in the esterification product mixture, released during the hydrogenation of the bis(3-methylcyclohexyl)methyl)cyclohexane-1,3-dicarboxylate, and produced as a by-product. In one embodiment of the invention, all or a portion of the (3-methylcyclohexyl)methanol that is contacted with the isophthalic acid is recycled from step (v) of the above process. In another embodiment, the amount of 3-MCHM in the hydrogenation product of step (iii) is sufficient to satisfy the (3-methylcyclohexyl)methanol required for the esterification reaction with isophthalic acid in step (i). In yet another embodiment, the above process is a continuous process.

As described above, the 3-MCHM may be recovered from the crude hydrogenation product from the second hydrogenation zone by distillation. It has been discovered that after distillation of the 3-MCHM from hydrogenation product from the second hydrogenation zone, the distillation bottoms can separate into a lower layer comprising a majority of the 1,3-cyclohexanedimethanol in the distillation bottoms and an upper layer comprising a majority of the 3,3'-oxybis(methylene)bis(methylcyclohexane) (III) and other impurities in the distillation bottoms. The term "majority," is intended to have its commonly accepted meaning of "the greater part." For example, the phrase "a majority of the 3,3'-oxybis(methylene)bis(methylcyclohexane) in the distillation bottoms" is intended to mean greater than half of the total amount of the 3,3'-oxybis(methylene)bis(methylcyclohexane) that is present in the distillation bottoms. The layers can be readily separated and 1,3-CHDM recovered and purified by a simple distillation of the lower layer. The upper layer, containing the 3-MCHM-diether and other impurities can be discarded or used in other applications. Our invention, therefore, provides a simplified method for the preparation and purification of the 1,3-CHDM. Hence, another embodiment of the invention is a process for the preparation of 1,3-cyclohexanedimethanol, comprising:

(i). contacting bis(3-methylcyclohexyl)methyl)isophthalate with hydrogen in a first hydrogenation zone in the presence of a catalyst effective for hydrogenation of an aromatic ring to produce a liquid effluent comprising bis(3-methylcyclohexyl)methyl)cyclohexane-1,3-dicarboxylate;

(ii). contacting the effluent from the first hydrogenation zone with hydrogen in the presence of an ester hydrogenation catalyst in a second hydrogenation zone to produce a hydrogenation product comprising 1,3-cyclohexanedimethanol, 3,3'-oxybis(methylene)bis(methylcyclohexane), and (3-methylcyclohexyl)methanol;

(iii). distilling the hydrogenation product from step (ii) to recover a distillate comprising a majority of the (3-methylcyclohexyl)methanol in the hydrogenation product and a distillation bottoms comprising a majority of the 1,3-cyclohexanedimethanol and 3,3'-oxybis(methylene)bis(methylcyclohexane) in the hydrogenation product;

(iv). allowing the distillation bottoms to form a lower layer comprising a majority of the 1,3-cyclohexanedimethanol in the distillation bottoms and a upper layer comprising a majority of the 3,3'-oxybis(methylene)bis(methylcyclohexane) in the distillation bottoms; and (v). separating the upper and lower layers of step (iv) and recovering the 1,3-cyclohexanedimethanol from the lower layer by distillation.

It should be understood that the above process comprises the various embodiments of the esterification process, hydrogenation steps, catalysts, temperature, pressure, reactor configurations, and products as described hereinabove in any combination.

For example, the bis(3-methylcyclohexyl)methyl)isophthalate may be produced by esterification of isophthalic acid with (3-methylcyclohexyl)methanol and can be hydrogenated by contacting with hydrogen at a temperature of about 150 to about 350° C. and a pressure of about 50 to about 400 bar gauge in the presence of a catalyst comprising palladium, platinum, nickel, ruthenium or combinations thereof deposited on a catalyst support material. In another embodiment of our process, the bis(3-methylcyclohexyl)methyl)isophthalate may be contacted with hydrogen at a temperature of about 180 to about 250° C. and a pressure of about 50 to about 170 bar gauge, the catalyst comprises palladium, ruthenium, or combinations thereof, and the catalyst support material comprises alumina, silica-alumina, titania, zirconia, chromium oxides, graphite, silicon carbide, or combinations thereof. In still another embodiment, the catalyst in step (i) comprises palladium on alumina.

The effluent from the first hydrogenation zone can be contacted with hydrogen at a temperature of 180 to about 300° C. at a pressure of about 40 to about 400 bar gauge in the presence of an ester hydrogenation catalyst comprising at least one Group VIII metal, a copper-containing catalyst, or a combination thereof. Some representative examples of the ester hydrogenation catalyst include copper chromite, copper oxide, Raney nickel, Raney cobalt, or combinations thereof. These catalysts may be optionally promoted with zinc, barium, calcium, manganese, magnesium, nickel, ruthenium, lanthanum, titanium, or a combination thereof.

As noted above, after distillation of the 3-MCHM from the hydrogenation product of step (ii) of the process, the distillation bottoms form an upper and lower layer wherein the lower layer comprises most of the 1,3-CHDM product that was present in the distillation bottoms and the upper layer comprises the majority of the 3,3'-oxybis(methylene)bis(methylcyclohexane) and other impurities in the distillation bottoms. For example, the lower layer comprises at least 50 weight percent of 1,3-cyclohexanedimethanol, based on the total weight of the lower layer. In another example, the upper layer comprises at least 70 weight percent of 3,3'-oxybis(methylene)bis(methylcyclohexane) based on the total weight of the upper layer. The 1,3-CHDM may be recovered from the lower layer by distillation.

The 3-MCHM that is recovered from the hydrogenation product in step (iii) of the process can be passed to a process for the preparation of bis(3-methylcyclohexyl)methyl)isophthalate by esterification of isophthalic acid. Recycling the 3-MCHM recovered in this manner utilizes by-products that are produced in the overall 1,3-CHDM process, avoids the introduction of additional materials such as, for example, alcohols that used for the preparation of isophthalate ester feedstocks, and simplifies the purification of the feedstocks and the final product. Another embodiment of our invention, therefore, is a process for the preparation of 1,3-cyclohexanedimethanol, comprising:

(i). feeding an esterification reaction product comprising bis (3-methylcyclohexyl)-methyl)isophthalate and (3-methylcyclohexyl)methanol with hydrogen to a first hydrogenation zone comprising a fixed bed of a palladium on alumina catalyst at a temperature of about 180° C. to about 250° C. and a pressure of about 50 to about 170 bar gauge to produce a liquid effluent comprising bis(3-methylcyclohexyl)methyl cyclohexane-1,3-dicarboxylate;

(ii). feeding the liquid effluent from step (i) with hydrogen to a second hydrogenation zone comprising a fixed bed comprising a copper chromite catalyst at a temperature of about 180 to about 300° C. and a pressure of about 100 to about 400 bar gauge to produce a hydrogenation product comprising 1,3-cyclohexanedimethanol, (3-methylcyclohexyl)methanol, and 3,3'-oxybis(methylene)bis(methylcyclohexane);

(iii). distilling the hydrogenation product from step (ii) to recover a distillate comprising a majority of the (3-methylcyclohexyl)methanol in the second hydrogenation product and a distillation bottoms comprising a majority of the 1,3-cyclohexanedimethanol and 3,3'-oxybis(methylene) bis(methylcyclohexane) in the hydrogenation product;

(iv). allowing the distillation bottoms to form a lower layer comprising a majority of the 1,3-cyclohexanedimethanol in the distillation bottoms and an upper layer comprising a majority of the 3,3'-oxybis(methylene)bis(methylcyclohexane) in the distillation bottoms;

(v). separating the upper and lower layers of step (iv) and recovering the 1,3-cyclohexanedimethanol from the lower layer by distillation; and (vi). passing the (3-methylcyclohexyl)methanol from the distillate in step (iii) to an esterification process to produce bis(3-methylcyclohexyl)methyl)isophthalate.

It is intended that the above process include the various embodiments of the esterification process, hydrogenation steps, catalysts, temperature, pressure, reactor configurations, and products as described hereinabove in any combination.

In one embodiment of the above process, for example, the lower layer comprises at least 50 weight percent of 1,3-cyclohexanedimethanol, based on the total weight of the lower layer. In another example, the upper layer contains 5 weight percent or less of 1,3-cyclohexanedimethanol, based on the total weight of the upper layer.

As noted previously, the upper layer contains the major portion of the 3-MCHM-diether, i.e., 3,3'-oxybis(methylene) bis(methylcyclohexane) (III), that was present in the distillation bottoms. For example, the upper layer may comprise at least 70 weight percent of 3,3'-oxybis(methylene)bis(methylcyclohexane) based on the total weight of the upper layer. In another example, the upper layer can comprise at least 80 weight percent of 3,3'-oxybis(methylene)bis(methylcyclohexane) based on the total weight of the upper layer.

The 3-MCHM that is recovered from the hydrogenation product in step (iii) of the process can be recycled by passing the recovered 3-MCHM to a process for the preparation of bis(3-methylcyclohexyl)methyl)isophthalate by esterification of isophthalic acid. In one embodiment of the process, the amount of 3-MCHM recovered in step (iii) is sufficient to prepare the entire esterification reaction product of step (i) that is required for the downstream 1,3-CHDM process.

The esterification, hydrogenation, and purification steps described hereinabove can be combined to form an integrated process for the preparation 1,3-CHDM from isophthalic acid in which the only exogenous feedstock is isophthalic acid. Yet another aspect of the instant invention, therefore, is a process for the preparation of a 1,3-cyclohexanedimethanol from isophthalic acid, comprising (i). contacting isophthalic acid and (3-methylcyclohexyl) methanol in a mole ratio of alcohol to acid of at least 2:1, in a reaction zone at a temperature of about 150° C. to about 280° C., while removing water from the reaction zone, to form an esterification product mixture comprising bis(3-methylcyclohexyl)methyl)isophthalate and unreacted (3-methylcyclohexyl)methanol;

(ii). contacting the esterification product mixture with hydrogen in a first hydrogenation zone in the presence of a catalyst effective for hydrogenation of an aromatic ring to produce a liquid effluent comprising bis(3-methylcyclohexyl)methyl)cyclohexane-1,3-dicarboxylate;

(iii). contacting the effluent from the first hydrogenation zone with hydrogen in the presence of an ester hydrogenation catalyst in a second hydrogenation zone to produce a hydrogenation product comprising 1,3-cyclohexanedimethanol, 3,3'-oxybis(methylene)bis(methylcyclohexane), and (3-methylcyclohexyl)methanol;

(iv). distilling the hydrogenation product from step (iii) to recover a distillate comprising a majority of the (3-methylcyclohexyl)methanol in the hydrogenation product and a distillation bottoms comprising a majority of the 1,3-cyclohexanedimethanol and 3,3'-oxybis(methylene)bis(methylcyclohexane) in the hydrogenation product;

(v). allowing the distillation bottoms to form an lower layer comprising a majority of the 1,3-cyclohexanedimethanol in the distillation bottoms and a upper layer comprising a majority of the 3,3'-oxybis(methylene)bis(methylcyclohexane) in the distillation bottoms;

(vi). separating the upper and lower layers of step (v) and recovering the 1,3-cyclohexanedimethanol from the lower layer by distillation; and (vii) recycling at least a portion of the (3-methylcyclohexyl) methanol from step (iv) to step (i).

The above process includes the various embodiments of the esterification process, hydrogenation steps, catalysts, temperature, pressure, reactor configurations, and products as described hereinabove in any combination.

In one embodiment, for example, the IPA and 3-MCHM are contacted in a reaction zone at a temperature of about 150 to about 280° C. Superatmospheric pressures may be used as need to prevent excessive vaporization of the esterification reaction mixture. Other examples of pressure and temperature that the esterification step may be operated at are about 180 to about 250° C., and about 190 to about 230° C. The molar ratio of alcohol to acid that can be used is typically at least 2:1. Some additional examples of molar ratios of alcohol to acid in the esterification step include about 2:1 to about 9:1; about 2:1 to about 8:1; about 2:1 to about 7:1; about 2:1 to about 5:1; about 2:1 to about 4:1; and about 2:1 to about 3:1.

The removal of the water may be accomplished by any conventional means known to persons skilled in the art such as, for example, distillation, membrane separation, the use of absorbents, or combinations thereof. In one embodiment of the process of the invention, the water for the esterification is removed from the reaction zone by distillation and step (i) further comprises recovering (3-methylcyclohexyl)methanol from the esterification product mixture by distillation and recycling to the reaction zone of step (i). In one embodiment, for example, the water and/or the 3-MCHM may be removed by distillation of a water/3-MCHM azeotrope, followed by separation of the water and 3-MCHM layers. The water may be removed from the process and the 3-MCHM returned or recycled to the esterification reaction zone of step (i).

The esterification reaction may be carried in the presence or absence of an exogenous esterification catalyst, i.e., a catalyst other than isophthalic acid, that is added to the reaction mixture for the purpose of increasing the rate of the esterification reaction. Any esterification catalyst that is known in art may be used. For example, the IPA and 3-MCHM can be contacted in the presence of a catalyst comprising compounds of titanium, magnesium, aluminum, boron, silicon, tin, zirconium, zinc, antimony, manganese, calcium, vanadium, sulfuric acid, p-toluene sulfonic acid, methane sulfonic acid, or phosphoric acid. Although the esterification process may be carried out in the presence of a catalyst, the reaction proceeds smoothly without added catalysts. Thus, in one embodiment of the invention, the IPA and 3-MCHM are contacted in the absence of an exogenous catalyst. Conducting the esterification reaction step in the absence of a catalyst avoids the need for additional purification steps to remove catalyst residues which can poison the hydrogenation catalysts or catalyze the formation of color bodies and other undesirable by-products in the subsequent steps of the instant process.

The hydrogenation product from the second hydrogenation zone comprises, in addition to other products, 3-MCHM that was present in the esterification product mixture, released during the hydrogenation of the bis(3-methylcyclohexyl)methyl)cyclohexane-1,3-dicarboxylate, and additionally produced as a by-product. All or a portion of this 3-MCHM can be recovered, by distillation for example, and recycled to the esterification step (i) of the process of the invention. In one embodiment of the invention, all or a portion of the (3-methylcyclohexyl)methanol that is contacted with the isophthalic acid is recycled from the hydrogenation product of the second hydrogenation zone. For example, the 3-MCHM recovered from the hydrogenation product can be combined with the 3-MCHM recovered the esterification product mixture and recycled back to the esterification reaction. In another embodiment, all of the 3-MCHM used in the esterification is recovered 3-MCHM from the hydrogenation product of the second hydrogenation zone.

The process of the present invention may be carried out in a batch, semi-continuous or continuous mode. In one example, continuous operation may involve continuously or intermittently feeding IPA and 3-MCHM to and continuously or intermittently removing alcohol, water and product-containing reaction mixture from a pressure vessel maintained at a predetermined temperature, pressure and liquid level; continuously passing the esterification product mixture to the first hydrogenation zone; continuously passing the effluent from the first hydrogenation zone to the second hydrogenation zone; continuously distilling the 3-MCHM from the hydrogenation product of the second hydrogenation zone; continuously allowing the distillation bottoms to separate into upper and lower layers; continuously separating the layers and distilling 1,3-CHDM from the lower layer; and continuously recycling the 3-MCHM recovered from the hydrogenation product back to the esterification step. It will be apparent to those skilled in the art that other reactor schemes may be used with this invention. For example, the esterification and hydrogenation reaction steps can be conducted in a plurality of reaction zones, in series, in parallel, or it may be conducted batch wise or continuously in a tubular plug flow reaction zone or series of such zones with recycle of unconsumed feed substrate materials if required. For example, the isophthalic acid and 3-MCHM can be contacted in a fixed bed or stirred reactor. As described hereinabove, the isophthalic acid also may be added incrementally to the reaction zone. In another example, the esterification reaction mixture may be fed to one or more secondary reaction vessels wherein conversion of IPA and/or IPA half-ester to the diester product is completed.

The esterification product mixture typically will comprise at least 50 weight percent of bis(3-methylcyclohexyl)methyl) isophthalate based on the total weight of the esterification product mixture. Other examples of weight percentages of bis(3-methylcyclohexyl)methyl)isophthalate in the esterification product mixture are at least 60 weight percent, at least 70 weight percent, at least 80 weight percent, and at least 90 weight percent.

Various embodiments of the first and second hydrogenation zone have been described above. For example, the esterification product mixture in step (ii) may be contacted with hydrogen at a temperature of about 150 to about 350° C. and a pressure of about 50 to about 400 bar gauge in the presence of a catalyst effective for hydrogenating an aromatic ring comprising palladium, platinum, nickel, ruthenium or combinations thereof deposited on a catalyst support material. In another example, the esterification product mixture in step (ii) is contacted with hydrogen at a temperature of about 180 to about 300° C. and a pressure of about 50 to about 170 bar gauge, and the catalyst effective for hydrogenating an aromatic ring comprises palladium, ruthenium, or combinations thereof, and the catalyst support material comprises alumina, silica-alumina, titania, zirconia, chromium oxides, graphite, silicon carbide, or combinations thereof. In yet another example, the catalyst effective for hydrogenating an aromatic ring comprises palladium on alumina.

The effluent from the first hydrogenation zone, comprising bis(3-methylcyclohexyl)methyl)cyclohexane-1,3-dicarboxylate (II), can be contacted with hydrogen at a temperature of 180 to about 300° C. at a pressure of about 40 to about 400 bar gauge in the presence of an ester hydrogenation catalyst comprising at least one Group VIII metal, a copper-containing catalyst, or a combination thereof. Some representative examples of ester hydrogenation catalysts include copper chromite, copper oxide, Raney nickel, Raney cobalt, or combinations thereof, and optionally promoted with zinc, barium, calcium, manganese, magnesium, nickel, ruthenium, or lanthanum.

Yet another embodiment of our novel 1,3-CHDM process is a process for the preparation of a 1,3-cyclohexanedimethanol from isophthalic acid, comprising (i). contacting isophthalic acid and (3-methylcyclohexyl) methanol in a mole ratio of alcohol to acid of about 2:1 to about 5:1, in a reaction zone at a temperature of about 150° C. to about 280° C. in the absence of a exogenous catalyst under super atmospheric pressure, while distilling water from the reaction zone, to form an esterification product mixture comprising bis(3-methylcyclohexyl)methyl) isophthalate and unreacted (3-methylcyclohexyl)methanol;

(ii). recovering unreacted (3-methylcyclohexyl)methanol from esterification product mixture by distillation to form a purified esterification product mixture and recycling the unreacted (3-methylcyclohexyl)methanol to the reaction zone of step (i);

(iii). contacting the purified esterification product mixture with hydrogen in a first hydrogenation zone in the presence of a palladium on alumina catalyst to produce a liquid effluent comprising bis(3-methylcyclohexyl)methyl)cyclohexane-1,3-dicarboxylate;

(iv). contacting the effluent from the first hydrogenation zone with hydrogen in the presence of a copper chromite catalyst in a second hydrogenation zone to produce a hydrogenation product comprising 1,3-cyclohexanedimethanol, 3,3'-oxybis(methylene)bis(methylcyclohexane), and (3-methylcyclohexyl)methanol;

(v). distilling the hydrogenation product from step (iv) to recover a distillate comprising a majority of the (3-methylcyclohexyl)methanol in the hydrogenation product and a distillation bottoms comprising a majority of the 1,3-cyclohexanedimethanol and 3,3'-oxybis(methylene)bis(methylcyclohexane) in the hydrogenation product;

(vi). allowing the distillation bottoms to form a lower layer comprising a majority of the 1,3-cyclohexanedimethanol in the distillation bottoms and an upper layer comprising a majority of the 3,3'-oxybis(methylene)bis(methylcyclohexane) in the distillation bottoms;

(vii). separating the upper and lower layers of step (vi) and recovering the 1,3-cyclohexanedimethanol from the lower layer by distillation; and (viii). recycling at least a portion of the (3-methylcyclohexyl) methanol from step (v) to the reaction zone of step (i).

It is understood that the above process comprises the various embodiments of the esterification process, hydrogenation steps, catalysts, temperature, pressure, reactor configurations, and products as described hereinabove in any combination.

In one embodiment, for example, the amount of 3-MCHM in the hydrogenation product of step (iv) is sufficient to satisfy the 3-MCHM required for the esterification reaction of step (i). In another embodiment, all or a portion of the 3-MCHM that is contacted with the isophthalic acid is recycled from the hydrogenation product of the second hydrogenation zone. For example, the 3-MCHM recovered from the hydrogenation product can be combined with the 3-MCHM recovered the esterification product mixture and recycled back to the esterification reaction. In another embodiment, all of the 3-MCHM used in the esterification is recovered 3-MCHM from the hydrogenation product of the second hydrogenation zone. In yet another embodiment, the above process may be operated entirely or in part as a continuous process.

Following distillation of the hydrogenation product from the second hydrogenation zone, the distillation bottoms separates into an upper layer comprising most of the 3-MCHM-diether and impurities that were present in the distillation bottoms and a lower layer comprising most of the 1,3-CHDM that was present in the distillation bottoms. For example, the upper layer can contain 10 weight percent or less of 1,3-cyclohexanedimethanol, based on the total weight of the upper layer. In another example, the upper layer can contain 5 weight percent or less of 1,3-cyclohexanedimethanol, based on the total weight of the lower layer. In another example, the upper layer can comprise at least 70 weight percent of 3,3'-oxybis(methylene)bis(methylcyclohexane) based on the total weight of the upper layer. In still another example, the upper layer can comprise at least 80 weight percent of 3,3'-oxybis (methylene)bis(methylcyclohexane) based on the total weight of the upper layer.

The invention also includes the following embodiments that are set forth in items 1-26 below:

1. A process for the preparation of a 1,3-cyclohexanedimethanol from isophthalic acid, comprising (i). contacting isophthalic acid and (3-methylcyclohexyl) methanol in a mole ratio of alcohol to acid of at least 2:1, in a reaction zone at a temperature of about 150° C. to about 280° C., while removing water from the reaction zone, to form an esterification product mixture comprising bis(3-methylcyclohexyl)methyl)isophthalate;

(ii). contacting the esterification product mixture with hydrogen in a first hydrogenation zone in the presence of a catalyst effective for hydrogenation of an aromatic ring to produce a liquid effluent comprising bis(3-methylcyclohexyl)methyl)cyclohexane-1,3-dicarboxylate;

(iii). contacting the effluent from the first hydrogenation zone with hydrogen in the presence of an ester hydrogenation catalyst in a second hydrogenation zone to produce a hydrogenation product comprising 1,3-cyclohexanedimethanol, 3,3'-oxybis(methylene)bis(methylcyclohexane), and (3-methylcyclohexyl)methanol, and;

(iv). recycling at least a portion of the (3-methylcyclohexyl) methanol from step (iii) to step (i).

2. A process that includes the embodiments of item 1, wherein the temperature of step (i) is about 190° C. to about 230° C.

3. A process that includes the embodiments of any one of items 1-2, wherein the ratio of alcohol to acid in step (i) is about 2:1 to about 5:1.

4. A process that includes the embodiments of any one of items 1-3, wherein the ratio of alcohol to acid in step (i) is about 2:1 to about 3:1.

5. A process that includes the embodiments of any one of items 1-4, wherein the water is removed from the reaction zone in step (i) by distillation.

6. A process that includes the embodiments of any one of items 1-5, wherein step (i) further comprises recovering (3-methylcyclohexyl)methanol the esterification product mixture by distillation.

7. A process that includes the embodiments of any one of items 1-6, wherein the isophthalic acid and (3-methylcyclohexyl)methanol are contacted in the absence of an exogenous catalyst.

8. A process that includes the embodiments of any one of items 1-7, wherein all or a portion of the (3-methylcyclohexyl)methanol that is contacted with the isophthalic acid is recycled from process for the preparation of 1,3-CHDM.

9. A process that includes the embodiments of any one of items 1-8, which is a continuous process.

10. A process that includes the embodiments of any one of items 1-9, wherein the esterification product mixture comprises at least 70 weight percent of bis(3-methylcyclohexyl) methyl)isophthalate.

11. A process that includes the embodiments of any one of items 1-10, which comprises contacting the isophthalic acid and (3-methylcyclohexyl)methanol in a fixed bed or stirred reactor.

12. A process that includes the embodiments of any one of items 1-11, wherein the isophthalic acid is added incrementally to the reaction zone.

13. A process that includes the embodiments of any one of items 1-12, wherein the (3-methylcyclohexyl)methanol in the hydrogenation product of step (iii) comprises (3-methylcyclohexyl)methanol that was present in the esterification product mixture, released during the hydrogenation of the bis(3-methylcyclohexyl)methyl)cyclohexane-1,3-dicarboxylate, and additionally produced as a by-product.

14. A process that includes the embodiments of any one of items 1-13, wherein the esterification product mixture in step (ii) is contacted with hydrogen at a temperature of about 150 to about 350° C. and a pressure of about 50 to about 400 bar gauge and the catalyst effective for hydrogenating an aromatic ring comprises palladium, platinum, nickel, ruthenium or combinations thereof deposited on a catalyst support material.

15. A process that includes the embodiments of any one of items 1-14, wherein the esterification product mixture in step (ii) is contacted with hydrogen at a temperature of about 160 to about 300° C. and a pressure of about 50 to about 170 bar gauge, the catalyst effective for hydrogenating an aromatic ring comprises palladium, ruthenium, or combinations thereof, and the catalyst support material comprises alumina, silica-alumina, titania, zirconia, chromium oxides, graphite, silicon carbide, or combinations thereof.

16. A process that includes the embodiments of any one of items 1-15, wherein the catalyst effective for hydrogenating an aromatic ring comprises palladium on alumina.

17. A process that includes the embodiments of any one of items 1-16, wherein the effluent from the first hydrogenation zone in step (iii) is contacted with hydrogen in step (ii) at a temperature of 180 to about 300° C. at a pressure of about 40 to about 400 bar gauge and the ester hydrogenation catalyst comprises at least one Group VIII metal, a copper-containing catalyst, or a combination thereof.

18. A process that includes the embodiments of any one of items 1-17, wherein the ester hydrogenation catalyst comprises copper chromite, copper oxide, Raney nickel, Raney cobalt, or combinations thereof, and optionally promoted with zinc, barium, calcium, manganese, magnesium, nickel, ruthenium, or lanthanum.

19. A process that includes the embodiments of any one of items 1-18, further comprising recovering the (3-methylcyclohexyl)methanol from the hydrogenation product in step (iii) by distillation.

20. A process that includes the embodiments of any one of items 1-19, wherein the (3-methylcyclohexyl)methanol contacted with IPA in step (i), recycled in step (iv), or a combination thereof, further comprises one or more additional alcohols having 4 to 20 carbon atoms.

21. A process that includes the embodiments of item 20, wherein the one or more additional alcohols comprise 1-butanol, 2-butanol, 2-ethylhexanol, cyclohexanol, benzyl alcohol, 1-hexanol, 1-pentanol, 1-octanol, 1-nonanol, 1-decanol, or combinations thereof.

22. A process that includes the embodiments of any one of items 1-21, wherein (i). the isophthalic acid and (3-methylcyclohexyl)methanol are contacted in a mole ratio of alcohol to acid of about 2:1 to about 5:1, in a reaction zone at a temperature of about 150° C. to about 280° C. in the absence of a exogenous catalyst under superatmospheric pressure, while removing water from the reaction zone, to form an esterification product comprising bis(3-methylcyclohexyl)methyl) isophthalate and unreacted (3-methylcyclohexyl)methanol;

(ii). the esterification product mixture is contacted with hydrogen in a first hydrogenation zone in the presence of a palladium on alumina catalyst to produce a liquid effluent comprising bis(3-methylcyclohexyl)methyl)cyclohexane-1,3-dicarboxylate;

(iii). the effluent from the first hydrogenation zone is contacted with hydrogen in the presence of a copper chromite catalyst in a second hydrogenation zone to produce a hydrogenation product comprising 1,3-cyclohexanedimethanol, 3,3'-oxybis(methylene)bis(methylcyclohexane), and (3-methylcyclohexyl)methanol;

(iv). the process further comprises (3-methylcyclohexyl) methanol from the hydrogenation product by distillation; and (v). at least a portion of the (3-methylcyclohexyl)methanol is recycled to step (i).

23. A process that includes the embodiments of item 22, wherein all or a portion of the (3-methylcyclohexyl)methanol is contacted with the isophthalic acid is recycled from step (v).

24. A process that includes the embodiments of any one of items 22-23, wherein the amount of (3-methylcyclohexyl) methanol in the hydrogenation product is sufficient to satisfy the (3-methylcyclohexyl)methanol required for step (i).

25. A process that includes the embodiments of any one of items 22-24, wherein the process is a continuous process.

26. A process that includes the embodiments of any one of items 22-25, wherein step (vi) further comprises
(a). distilling the hydrogenation product from step (iii) to recover a distillate comprising a majority of the (3-methylcyclohexyl)methanol in the hydrogenation product and a distillation bottoms comprising a majority of the 1,3-cyclohexanedimethanol and 3,3'-oxybis(methylene)bis(methylcyclohexane), in the hydrogenation product;
(b). allowing the distillation bottoms to form an lower layer comprising a majority of the 1,3-cyclohexanedimethanol in the distillation bottoms and a upper layer comprising a majority of the 3,3'-oxybis(methylene)bis(methylcyclohexane) in the distillation bottoms; and
(c). separating the upper and lower layers and recovering the 1,3-cyclohexanedimethanol from the lower layer by distillation.

EXAMPLES

The invention is further described and illustrated by the following prophetic examples.

Prophetic Example 1

Esterification of isophthalic acid with (3-methylcyclohexyl)methanol

IPA (0.5 mole), 3-MCHM (2.0 moles), and 900 ppm of a Ti catalyst were charged to a 500 mL round-bottomed flask equipped with a distillation column and receiver (IPA:3-MCHM molar ratio of 4:1) and stirred at 200° C. at atmospheric pressure for 1 hour and 38 minutes with water removal by distillation. During the course of the reaction, the reaction mixture changed from a slurry to a clear solution. No analytical data was collected.

Prophetic Example 2

Esterification of isophthalic acid with (3-methylcyclohexyl)methanol

The reaction of Example 1 was repeated except that no catalyst was added to the reaction mixture and the reaction mixture was stirred at 200° C. for 5 hours. At the end of the reaction period, a clear solution was obtained. The conversion of IPA was 90% by proton NMR.

Prophetic Example 3

Esterification of isophthalic acid with (3-methylcyclohexyl)methanol

The reaction of Example 2 was repeated except that the reaction mixture was stirred at 200° C. for 23 hours. At the end of the reaction period, a clear solution was obtained. The conversion of IPA was 99% by proton NMR.

Prophetic Example 4

Esterification of isophthalic acid with (3-methylcyclohexyl)methanol

The reaction of Example 2 was repeated except that 0.5 moles of IPA and 1.5 moles of 3-MCHM were charged to the reaction vessel and the reaction mixture was stirred at 200° C. for 7 hours. At the end of the reaction period, a clear solution was obtained. The conversion of IPA was 94% by proton NMR.

Prophetic Example 5

Batch hydrogenation of bis(3-methylcyclohexyl) methyl)isophthalate to bis(3-methylcyclohexyl)methyl)cyclohexane-1,3-dicarboxylate ("1,3-DXCD")

bis(3-methylcyclohexyl)methyl)isophthalate (abbreviated herein as "DXI") was hydrogenated in a batch autoclave. DXI starting material was dissolved in 1,4-dimethycyclohexanedicarboxylate (abbreviated herein as "DMCD") at a concentration of 20% by weight. This mixture (220 g) was loaded into a batch autoclave with 10 g of $Pd/Al_2O_3$ catalyst and hydrogenated for 1 hour at 124.1 bar gauge (1800 psig) and 200° C. Samples of the feed material and final product material were collected and analyzed by gas chromatography. The feed samples and reaction products and effluents were analyzed by capillary gas-liquid chromatography ("GC") using an Agilent Model 6890, or equivalent gas chromatograph equipped with a thermal conductivity detector. Results are given as area percentages. The GC samples (1 microliter) were injected without dilution onto a 0.50 micron (30 m×0.25 mm) DB-WAX column using a helium carrier gas. The GC column temperature was maintained at 100° C. for 2 minutes, then programmed to 240° C. at 16° C. per minute. The final temperature of 240° C. was held for 20 minutes. The injection port used a 100:1 split ratio. The conversion of DXI to 1,3-DXCD was 97%.

Prophetic Example 6

Batch hydrogenation of bis(3-methylcyclohexyl) methyl)cyclohexane-1,3-dicarboxylate to 1,3-cyclohexanedimethanol ("1,3-CHDM")

1,3-DXCD was hydrogenated at 4100 psi and 250° C. with 40 g of CuCr catalyst for 5 hours. Approximately 95% of the starting 1,3-DXCD was converted to 1,3-CHDM during this period. Both 1,3-CHDM and 3-MCHM are coproduced during the reaction.

Prophetic Example 7

Continuous hydrogenation of DXT to DXCD

The DXT material was continuously hydrogenated in a fixed bed reactor system at 137.9 bar gauge (2000 psig) and 200° C. The experiments were carried out in a continuous mode of operation utilizing a vertical trickle bed reactor having a length of 72 inches and an inside diameter of 1 inch as the reactor. The reactor temperature was measured with a series of 10 thermocouples inserted into the wall of the reactor. The reactor was loaded with 750 mL of a low-acidity $Pd/\alpha-Al_2O_3$ catalyst extrudates.

In order to achieve a high conversion, the material was processed twice through the reactor. On the first pass, fresh material was fed at a rate of 0.6 L/hr. with a 10:1 recycle rate. The product of the first pass was then collected and fed to the reactor again at a rate of 1.8 L/hr. with no recycle. The product of the second pass was essentially 100% conversion of the DXI to 1,3-DXCD. The overall yield to 1,3-DXCD was better than 98% overall yield.

Prophetic Example 8

Hydrogenolysis of DXCD to 1,3-CHDM

The product of the hydrogenation in Example 7 was reacted further to produce 1,3-CHDM. This reaction was performed continuously in a trickle bed reactor at 225° C. and 344.7 bar gauge (5000 psig) using CuCr as a catalyst. Following activation, feed was introduced to the reactor at a rate of 1.5 L/hr. with 8:1 recycle. As with the first step hydrogenation, the product was collected and processed through the reactor a second time in order to achieve complete conversion. At the end of two passes, the conversion of DXCD to 1,3-CHDM was 97%.

Prophetic Example 9

Purification of 1,3-CHDM from hydrogenation of DXCD

Crude final product, comprising 3-MCHM, 1,3-CHDM, 3-MCHM-diether, and other various byproducts was isolated from a continuous hydrogenolysis run. The crude product was analyzed by gas chromatography is shown below (trace impurities excluded for simplicity). Three isomers of the 3-MCHM-diether can be seen in the gas chromatograph because of the cis/trans isomers of the cyclohexane ring. The total concentrations in area percent were as follows:

| | |
|---|---|
| 3-MCHM | 81.4% |
| 1,3-CHDM | 13.1% |
| 3-MCHM diethers | 6.0% |
| Other impurities | 1.8% |

The above crude product was subjected to distillation to remove the excess 3-MCHM. This was accomplished on a vacuum still consisting of a one-liter flask, magnetic stir bar, two 10" Penn State packed columns with feed port between the columns, a needle valve for feeding material, feed tank, vapor take-off head, magnetic for lifter, condenser on vapor take-off head, condenser for receiving material, fraction cutter, receiver, three thermometers (base, feed, take-off vapor), and magnetic stirrer. The distillation system was operated at about 10 torr, a base temperature of about 150-160° C., and a take-off temperature of about 80 to about 100° C.; the a top take-off ratio was set a 35%. A total of 5702.1 of 3-MCHM was recovered.

Very little 1,3-CHDM was lost to the recovered 3-MCHM. After the distillation was complete, two phases formed in the base. The phases were separated to give 804 g of a bottom layer and 314.1 g of a top layer. The composition of each layer is summarized in Table 1.

TABLE 1

| Bottom Layer | Top Layer |
|---|---|
| 1,3-CHDM: 91.7% | 1,3-CHDM: 2.4% |
| 3-MCHM diether: 4.1% | 3-MCHM diether: 88.9% |
| 4.2% other impurities | 8.7% other impurities |

The bottom layer was distilled to remove 3-MCHM diether using a two-liter round bottom flask, stir bar, thermometer, 10" Penn state packed column, magnetic take-off head, condenser, fraction cutter, and take-off receiver. The base was charged with the bottom layer from the phase-separated mixture. The mixture was distilled at 10 torr at a base temperature of 165-170° C. and a take-off temperature of about 140-160° C.

After the ether removal step, the magnetic take-off head was removed and replaced with a 3" Vigreux column and heat tape applied to take-off line to keep 1,3-CHDM melted until collected. A total of 709.4 grams of 1,3-CHDM was collected.

We claim:

1. A process for the preparation of a 1,3-cyclohexanedimethanol from isophthalic acid, comprising:
    (i). contacting isophthalic acid and (3-methylcyclohexyl)methanol in a reaction zone at a temperature of about 150° C. to about 280° C. while removing water from the reaction zone, to form an esterification product mixture comprising bis(3-methylcyclohexyl)methyl)isophthalate;
    (ii). contacting the esterification product mixture with hydrogen in a first hydrogenation zone in the presence of a catalyst effective for hydrogenation of an aromatic ring to produce a liquid effluent comprising bis(3-methylcyclohexyl)methyl)cyclohexane-1,3-dicarboxylate;
    (iii). contacting the effluent from the first hydrogenation zone with hydrogen in the presence of an ester hydrogenation catalyst in a second hydrogenation zone to produce a hydrogenation product comprising 1,3-cyclohexanedimethanol, 3,3'-oxybis(methylene)bis(methylcyclohexane), and (3-methylcyclohexyl)methanol and;
    (iv). recycling at least a portion of the (3-methylcyclohexyl)methanol from step (iii) to step (i).

2. The process according to claim 1, wherein the temperature of step (i) is about 190° C. to about 230° C.

3. The process according to claim 1, wherein the ratio of alcohol to acid in step (i) is about 2:1 to about 5:1.

4. The process according to claim 1, wherein the ratio of alcohol to acid in step (i) is about 2:1 to about 3:1.

5. The process according to claim 1, wherein the water is removed from the reaction zone in step (i) by distillation.

6. The process according to claim 1, wherein step (i) further comprises recovering unreacted (3-methylcyclohexyl)methanol from the esterification product mixture by distillation.

7. The process according to claim 1, wherein the isophthalic acid and (3-methylcyclohexyl)methanol are contacted in the absence of an exogenous catalyst.

8. The process according to claim 1, wherein all or a portion of the (3-methylcyclohexyl)methanol that is contacted with the isophthalic acid is recycled from process for the preparation of 1,3-cyclohexanedimethanol.

9. The process according to claim 1, which is a continuous process.

10. The process according to claim 1, wherein the esterification product mixture comprises at least 70 weight percent of bis(3-methylcyclohexyl)methyl)isophthalate.

11. The process according to claim 1, which comprises contacting the isophthalic acid and (3-methylcyclohexyl)methanol in a fixed bed or stirred reactor.

12. The process according to claim 1, wherein the isophthalic acid is added incrementally to the reaction zone.

13. The process according to claim 1, wherein the (3-methylcyclohexyl)methanol in the hydrogenation product of step (iii) comprises (3-methylcyclohexyl)methanol that was present in the esterification product mixture, released during the hydrogenation of the bis(3-methylcyclohexyl)methyl)cyclohexane-1,3-dicarboxylate, and additionally produced as a by-product.

14. The process according to claim 1, wherein the esterification product mixture in step (ii) is contacted with hydrogen at a temperature of about 150 to about 350° C. and a pressure of about 50 to about 400 bars gauge and the catalyst effective for hydrogenating an aromatic ring comprises palladium, platinum, nickel, ruthenium or combinations thereof deposited on a catalyst support material.

15. The process according to claim 1, wherein the esterification product mixture in step (ii) is contacted with hydrogen at a temperature of about 160 to about 300° C. and a pressure of about 50 to about 170 bars gauge, the catalyst effective for hydrogenating an aromatic ring comprises palladium, ruthenium, or combinations thereof, and the catalyst support material comprises alumina, silica-alumina, titania, zirconia, chromium oxides, graphite, silicon carbide, or combinations thereof.

16. The process according to claim 1, wherein the catalyst effective for hydrogenating an aromatic ring comprises palladium on alumina.

17. The process according to claim 1 wherein the effluent from the first hydrogenation zone in step (iii) is contacted with hydrogen in step (ii) at a temperature of 180 to about 300° C. at a pressure of about 40 to about 400 bars gauge and the ester hydrogenation catalyst comprises at least one Group VIII metal, a copper-containing catalyst, or a combination thereof.

18. The process according to claim 1, wherein the ester hydrogenation catalyst comprises copper chromite, copper oxide, Raney nickel, Raney cobalt, or combinations thereof, and optionally promoted with zinc, barium, calcium, manganese, magnesium, nickel, ruthenium, or lanthanum.

19. The process according to claim 1, further comprising recovering the (3-methylcyclohexyl)methanol from the hydrogenation product in step (iii) by distillation.

20. The process according to claim 1, wherein, wherein the (3-methylcyclohexyl)-methanol contacted with isophthalic acid in step (i), recycled in step (iv), or a combination thereof, further comprises one or more additional alcohols having 4 to 20 carbon atoms.

21. The process according to claim 20, wherein the one or more additional alcohols comprise 1-butanol, 2-butanol, 2-ethylhexanol, cyclohexanol, benzyl alcohol, 1-hexanol, 1-pentanol, 1-octanol, 1-nonanol, 1-decanol, or combinations thereof.

22. A process for the preparation of 1,3-cyclohexanedimethanol from isophthalic acid, comprising:
(i). contacting isophthalic acid and (3-methylcyclohexyl)methanol in a mole ratio of alcohol to acid of about 2:1 to about 5:1, in a reaction zone at a temperature of about 150° C. to about 280° C. in the absence of a exogenous catalyst, while removing water from the reaction zone, to form an esterification product mixture comprising bis(3-methylcyclohexyl)methyl)isophthalate and unreacted (3-methylcyclohexyl)methanol;
(ii). contacting the esterification product mixture with hydrogen in a first hydrogenation zone in the presence of a palladium on alumina catalyst to produce a liquid effluent comprising bis(3-methylcyclohexyl)methyl)cyclohexane-1,3-dicarboxylate;
(iii). contacting the effluent from the first hydrogenation zone with hydrogen in the presence of a copper chromite catalyst in a second hydrogenation zone to produce a hydrogenation product comprising 1,3-cyclohexanedimethanol, 3,3'-oxybis(methylene)bis(methylcyclohexane), and (3-methylcyclohexyl)methanol;
(iv). recovering the (3-methylcyclohexyl)methanol from the hydrogenation product by distillation; and
(v). recycling at least a portion of the (3-methylcyclohexyl)methanol to step (i).

23. The process according to claim 22, wherein all or a portion of the (3-methylcyclohexyl)methanol is contacted with the isophthalic acid is recycled from step (v).

24. The process according to claim 22, wherein the amount of (3-methylcyclohexyl)methanol in the hydrogenation product is sufficient to satisfy the (3-methylcyclohexyl)methanol required for step (i).

25. The process according to claim 22, which is a continuous process.

26. The process according to claim 22, wherein step (vi) further comprises:
(a). distilling the hydrogenation product from step (iii) to recover a distillate comprising a majority of the (3-methylcyclohexyl)methanol in the hydrogenation product and a distillation bottoms comprising a majority of the 1,3-cyclohexanedimethanol, 3,3'-oxybis(methylene)bis(methylcyclohexane), and other impurities in the hydrogenation product;
(b). allowing the distillation bottoms to form an lower layer comprising a majority of the 1,3-cyclohexanedimethanol in the distillation bottoms and a upper layer comprising a majority of the 3,3'-oxybis(methylene)bis(methylcyclohexane) and other impurities in the distillation bottoms; and
(c). separating the upper and lower layers and recovering the 1,3-cyclohexanedimethanol from the lower layer by distillation.

* * * * *